US010508251B2

(12) United States Patent
Lofquist

(10) Patent No.: US 10,508,251 B2
(45) Date of Patent: Dec. 17, 2019

(54) PREPARATION OF VEGETABLE-BASED STEARIC ACID

(71) Applicant: MIG Acquisition LLC, Chicago, IL (US)

(72) Inventor: Eric E. Lofquist, Novelty, OH (US)

(73) Assignee: MIG Acquisition LLC, Chicago, IL (US)

( * ) Notice: Subject to any disclaimer, the term of this patent is extended or adjusted under 35 U.S.C. 154(b) by 0 days.

(21) Appl. No.: 16/251,180

(22) Filed: Jan. 18, 2019

(65) Prior Publication Data

US 2019/0225912 A1    Jul. 25, 2019

Related U.S. Application Data

(60) Provisional application No. 62/619,148, filed on Jan. 19, 2018.

(51) Int. Cl.
| | |
|---|---|
| *C11B 1/04* | (2006.01) |
| *C07C 53/126* | (2006.01) |
| *C11B 15/00* | (2006.01) |
| *C11B 3/14* | (2006.01) |
| *C07C 51/36* | (2006.01) |
| *C07C 51/43* | (2006.01) |
| *C07C 51/44* | (2006.01) |
| *C11C 1/02* | (2006.01) |
| *C11C 1/04* | (2006.01) |
| *C11C 1/10* | (2006.01) |
| *C11C 3/12* | (2006.01) |

(52) U.S. Cl.
CPC ............ *C11B 1/04* (2013.01); *C07C 51/36* (2013.01); *C07C 51/43* (2013.01); *C07C 51/44* (2013.01); *C07C 53/126* (2013.01); *C11B 3/14* (2013.01); *C11B 15/00* (2013.01); *C11C 1/025* (2013.01); *C11C 1/04* (2013.01); *C11C 1/10* (2013.01); *C11C 3/12* (2013.01)

(58) Field of Classification Search
CPC ... C11B 1/04; C11B 3/14; C11B 15/00; C11C 1/025; C11C 1/04; C11C 1/10; C11C 3/12; C07C 51/36; C07C 51/43; C07C 53/126
USPC ........................................................ 554/205
See application file for complete search history.

(56) References Cited

U.S. PATENT DOCUMENTS 1,659,790 A  *  2/1928  Starrels ..................... C11C 1/02
                                                        554/142

* cited by examiner

*Primary Examiner* — Deborah D Carr
(74) *Attorney, Agent, or Firm* — Ice Miller LLP

(57) ABSTRACT

One or more techniques are disclosed for a process of preparing a concentrated form of a vegetable-based stearic acid from a plant source. The process may comprise drying and deodorizing a vegetable based emulsion; and further concentrating the resulting fatty acid and triglyceride mix. The process may further comprise distillation of the resulting concentrated fatty acid and triglyceride mix, to separate the free fatty acids from the triglycerides. Additionally, the process may comprise fractional distillation of the free fatty acid distillate, to produce a concentrated from of the stearic acid, separating it from other fatty acids.

20 Claims, 3 Drawing Sheets

PREPARATION OF VEGETABLE-BASED STEARIC ACID

RELATED APPLICATIONS

This application claims priority to U.S. Ser. No. 62/619,148, entitled PREPARATION OF VEGETABLE-BASED STEARIC ACID, filed Jan. 19, 2018, which is incorporated herein by reference.

BACKGROUND

Stearic acid (also known as octadecanoic acid) is a saturated fatty acid with an 18-carbon chain. Stearic acid may be found in fats and oils from both animals and plants. Stearic acid may be used in a variety of applications, including but not limited to food products, animal products, personal care products, candles, fireworks, and plastics manufacturing as a lubricant and release agent. Stearic acid can be prepared like most fatty acids. The typical steps involved in the manufacture of stearic acid may include: hydrolysis of a fat or oil to produce a mixture of fatty acids and glycerine; separation of the fatty acids and glycerine; and purification and separation of fatty acid mixtures into two or more fatty acid mixtures.

Palmitic acid (also known as hexadecanoic acid) is a saturated fatty acid with a 16-carbon chain. Palmitic acid may be found in fats and oils from both animals and plants. Palmitic acid may be used in a variety of applications, including but not limited to food products, animal products, personal care products, and release agents. Palmitic acid can be prepared like most fatty acids, such as those described above for stearic acid.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One or more techniques are disclosed for a process of preparing stearic acid from a plant-based source may comprise drying a vegetable-based fat emulsion resulting in a fatty acid and triglyceride mix. Further, the process can comprise distilling the fatty acid and triglyceride mix to substantially separate the triglycerides from free fatty acids. Additionally, the process can comprise separating the free fatty acids into one or more types of fatty-acids, resulting in a concentrated fatty acid vegetable-based stearic acid product. In some implementations, the process may also comprise concentrating the fatty acid and triglyceride mix; separating the free fatty acids using fractional distillation; and/or prilling of the resulting product to produce a prilled, fractionated vegetable-based fatty acid. In some implementations, the vegetable-based fat emulsion can comprise co-products from plant sources as a feedstock from another process. In some implementations, the process may also include distilling the stearic acid product to provide palmitic acid and/or a fully hydrogenated fatty acid.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein.

DETAILED DESCRIPTION

Figure 1:
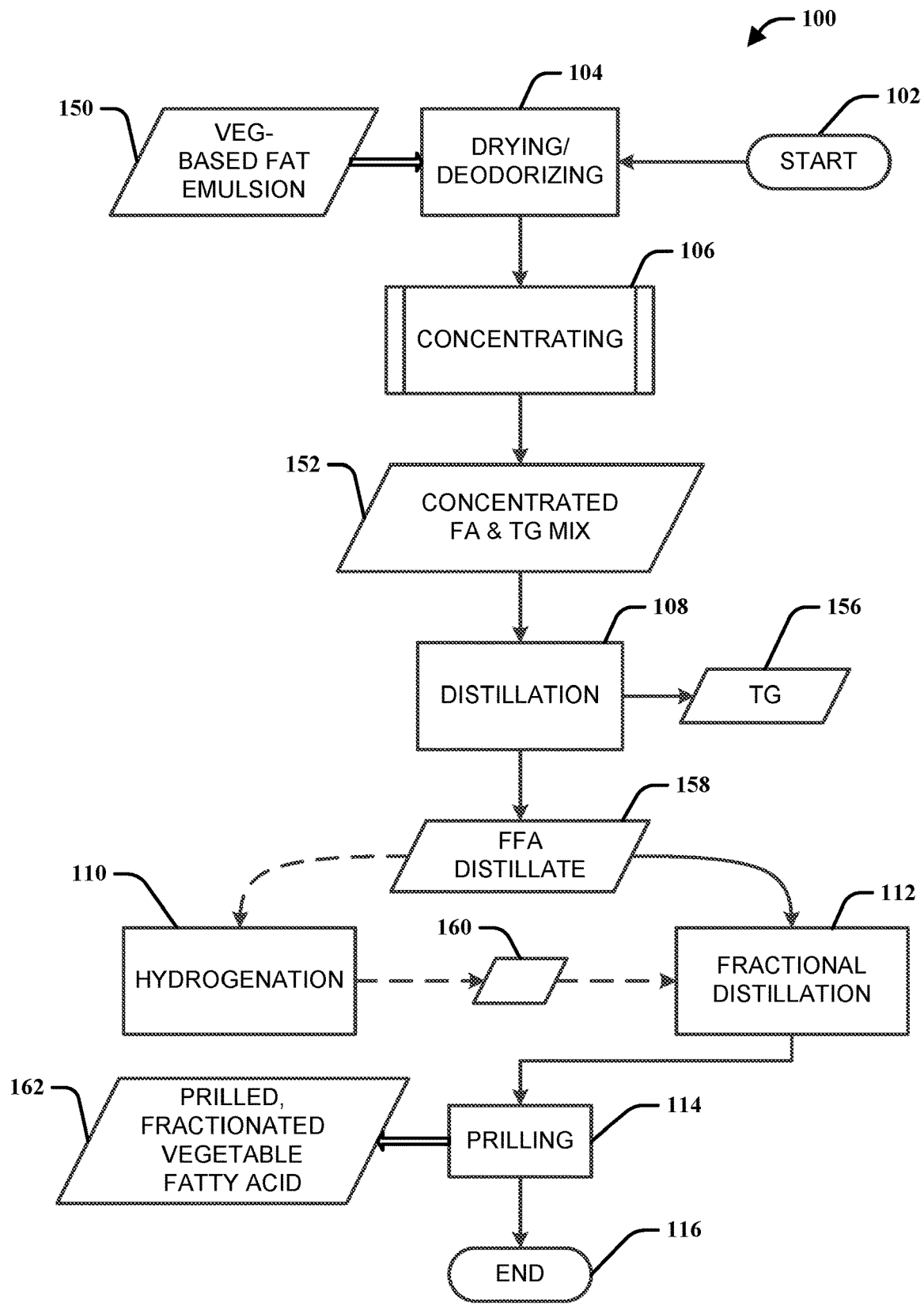
FIG. 1 is a flow diagram illustrating an exemplary method for producing vegetable fatty acid.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

Stearic acid is an eighteen-carbon chain fatty acid, and is also known as octadecanoic acid (its IUPAC designation). Stearic acid is typically disposed as a hard, wax-like material, which can be produced in various grades, for example, depending on an intended application or use. For example, stearic acid may be used in rubber products, pharmaceuticals, cosmetics, food packaging, soap, detergents, surfactants, coatings, lubricants, food products, and textiles. Some forms of stearic acid can be utilized in animal feed products, and/or supplements.

In one aspect, a method may be devised for producing a vegetable-based fatty acid, for example, which may be used in in animal feed products and supplements. As one example, typical manufacturing stearic acid can comprise hydrolysis (e.g., also known as saponification) of a fat or oil to produce a mixture of fatty acids and glycerine. In this example, the mixture of fatty acids and glycerine may be separated (e.g., also called Acidulation). Additionally, the resulting fatty acid stream can be purified and separated into two or more fatty acids streams. In one implementation, the purification and separation process may include distillation. Other methods used to produce stearic and other fatty acids may include solvent crystallization, hydrogenation, and distillation, for example.

In one implementation, in this aspect, stearic acid may be produced by: 1) drying and deodorizing a feedstock fat and/or oil; 2) concentrating the resulting dried and deodorized mix; 3) distilling the concentrated mix, and 4) further distilling and/or hydrogenating the fatty acid to produce a stearic acid. In the processes described herein, for example, stearic acid, palmitic acid, and fully hydrogenated fatty acid may be produced from different sources of fat and/or oil (e.g., soybean oil, corn oil; palm oil; coconut oil; and/or canola oil), and may also be produced without the use of hydrolysis.

FIG. 1 is a flow diagram illustrating one exemplary embodiment of a method 100 for producing vegetable fatty acids from a vegetable-based fat feedstock. The exemplary method 100 begins at 102. At 104, a feedstock of a vegetable-based fat emulsion 150 is introduced to a drying and deodorizing process. In one implementation, the vegetable-based fat emulsion feedstock may not consistently comprise the same ingredients, and/or in the same proportions. As an example, the vegetable-based fat emulsion feedstock can be provided from a variety of sources, such as from the refining and manufacturing of vegetable-based products (e.g., oils, such as soybean oil, corn oil; palm oil; coconut oil; and/or canola oil) as a vegetable oil-based feedstock, and/or from a vegetable-based feedstock (e.g., vegetative matter, seeds, fruits, flowers, roots, etc.).

For example, the manufacturing and/or refining of vegetable-based oils can result in the production of a co-product of the refining/manufacturing process. A co-product may comprise at least a portion of the resulting production stream that is not part of the target end-product (e.g., refined vegetable oil). In this example, the co-product of such a process may comprise at least a portion of the feedstock of a vegetable-based fat emulsion 150. As another example, at least a portion of the source of the vegetable-based fat emulsion may include fat resulting from processing of vegetative matter, such as seeds, vegetables, fruits, flowers, grasses, and other vegetation. Further, as an example, at least a portion of the source of the vegetable-based fat emulsion may include fat resulting from a surplus source, or a co-product that may typically be disposed of or discarded. In one implementation, the source fat may be a non-conforming result of a process to make other products (e.g., does not meet target specifications). As an example, one or more portions of a vegetable-based fat emulsion feedstock can comprise products resulting from manufacture or refining of: soybean oil; corn oil; palm oil; coconut oil; and/or canola oil; such as from other vegetative matter.

As described above, in one implementation, the feedstock of the vegetable-based fat emulsion 150 can comprise a varied composition. That is, for example, the composition of the ingredients and/or proportions of said ingredients may vary for respective batches (e.g., or periodically for a continuous feed process), which may be dependent upon the feedstock source, and/or the amount or type of products comprising the feedstock. As an example, the feedstock can comprise an oil portion, a water portion, and one or more types of free fatty acids. Further, for example, the sources of the one or more components of the vegetable-based fat emulsion 150 can comprise products that are approved as animal food grade products (e.g., as provided for under a governing authority, such as the FDA). In an example, the one or more components of the vegetable-based fat emulsion 150 can comprise a co-product from production of food-grade vegetable oils and/or vegetable-based products. Additionally, in one implementation, the one or more components of the vegetable-based fat emulsion 150 can comprise merely organic products.

In one implementation, the vegetable-based fat emulsion 150 can comprise from about five percent to about thirty percent of palmitic acid in an oil portion. In one implementation, the vegetable fat emulsion 150 can comprise from about five percent to about ten percent of palmitic acid in the oil portion. In one implementation, the vegetable fat emulsion 150 can comprise from about ten percent to about fifteen percent of palmitic acid in the oil portion. In one implementation, the vegetable fat emulsion 150 can comprise from about fifteen percent to about twenty percent of palmitic acid in the oil portion. In one implementation, the vegetable fat emulsion 150 can comprise from about twenty percent to about twenty-five percent of palmitic acid in the oil portion. In one implementation, the vegetable fat emulsion 150 can comprise from about twenty-five percent to about thirty percent of palmitic acid in the oil portion.

In one implementation, the vegetable fat emulsion 150 can comprise from about seventy percent to about ninety-five percent of steric acid in an oil portion. In one implementation, the vegetable fat emulsion 150 can comprise from about seventy percent to about seventy-five percent of steric acid in an oil portion. In one implementation, the vegetable fat emulsion 150 can comprise from about seventy-five percent to about eighty percent of steric acid in an oil portion. In one implementation, the vegetable fat emulsion 150 can comprise from about eighty percent to about eighty-five percent of steric acid in an oil portion. In one implementation, the vegetable fat emulsion 150 can comprise from about eighty-five percent to about ninety percent of steric acid in an oil portion.

In one implementation, the remaining portion of the vegetable fat emulsion 150 can comprise one or more of: water, free fatty acids, and other triglycerides.

Returning to FIG. 1, in one implementation, the drying and deodorizing process, at 104 can comprise removal of water and/or light-end products from the vegetable-based fat emulsion 150. In this implementation, the drying and deodorizing process for vegetable fats can also be used to remove odor causing substances, such as odorous light end products. As an example, the vegetable fat emulsion 150 can be subjected to a steam distillation under an appropriate temperature and vacuum, in order to evaporate water and potential odor causing substances. In this implementation, the resulting product is dryer vegetable fat with less odor.

As an example, due to potential sensitivity of fatty acids to heat, the drying and deodorizing distillation may be conducted at an appropriate temperature that is practical for the desired product and process, balanced with a practical time for the fatty acid disposed in the distillation unit. Often, a distillation process may balance application of a vacuum (e.g., a partial vacuum imparting low pressure, up to a substantially full vacuum imparting higher pressure), practical heating, and short contact times, which can be based on the type of source fatty acid (e.g., type of oil, co-product, fatty acid content, etc.), and the desired specification of resulting distilled fatty acid. In one implementation, distillation may occur at about 250° F. (120° C.) to about 300° F. (148° C.). In another implementation, the distillation may occur under a partial vacuum. In another implementation, the distillation under a partial vacuum may have a pressure of about 5 mm Hg or less. In one implementation, the moisture content may be reduced to about less than one percent (1%). In one implementation, the moisture content may be reduced to about 0.3% by weight or less. In another implementation, the moisture content may be reduced to about 0.2% by weight or less.

In one implementations, such as a batch drying and deodorization distillation at atmospheric pressure, a distillation pot can be charged with the vegetable fat emulsion 150, and heated to a range of 260° to 316° C. (e.g., 500° to 601° F.). Further, in some implementations, the drying and deodorization distillation may include processing at a reduced pressure, such as a range of five to fifty millimeters of mercury (5-50 mm Hg), and the vegetable fat emulsion 150 can be heated to a range of 200° to 350° F. (e.g., 93° to 177° F.). In another implementation, the drying and deodorization distillation may be performed under very low pressure (e.g., as high a vacuum as practicable), and the vegetable fat emulsion 150 can be heated to a range of 400° to 500° F. (e.g., 204° to 260° C.).

In other implementation such as continuous drying and deodorization distillation, a preheated vegetable fat emulsion can be fed through a series of heated reaction chambers, for example, which may be further heated by steam. In this implementation, a low pressure (e.g., partial vacuum) can be applied to a reaction chamber, and the temperature of the feed can produce a substantially instantaneous distillation of the vegetable fat emulsion. In this implementation, a partial vacuum can be maintained at a range of approximately thirty to thirty-five mm Hg, at a temperature from 196° to 260° F. (e.g., 91° to 127° C.). As an example, the fatty acids may be disposed in the reaction chambers for about thirty minutes. In other implementations, different fatty acid distillation methods may be employed, which are well known in the art, such as fractional distillation, reactive distillation, and molecular distillation.

In this example implementation, the dried and deodorized vegetable fat emulsion resulting of the drying and deodorization, at 104, can be subjected to additional concentration, at 106. In one implementation, the concentration of the dried and deodorized vegetable fat emulsion may occur through a vacuum distillation process. As an example, the vacuum distillation process may occur under a vacuum in a range of less than ten (10) mm Hg to about one-hundred and eighty (180) mm Hg. In one implementation, the vacuum distillation concentration may occur at a temperature at least about 400° F. (200° C.); however, for example, the temperature may be disposed in a range of about 196° F. to 500° F. (e.g., 91° to 260° C.), depending on the desired moisture content, length of exposure, and/or the amount of vacuum applied.

In another implementation, a distillation tower or distillation column may be used for the additional concentration, at 106. In another implementation, a vapor stream condensation may be used to concentrate the fatty acids, at 106. In one implementation, the resulting product of the concentration can comprise a concentrated mix of fatty acids and triglycerides 152. As one example, the concentrated mix of fatty acids and triglycerides 152 can comprise at least about 90% fatty acids. In another implementation, the concentrated mix of fatty acids and triglycerides 152 can comprise at least about 96% of fatty acids. The concentrated mix of fatty acids and triglycerides 152 may comprise a plant-based fatty acid product. In one implementation, the concentration of the fatty acids, at 106, can comprise a continuous process; or, alternately, through a batch process.

In FIG. 1, at 108, the concentrated mix of fatty acids and triglycerides 152 can be subjected to separation distillation (e.g., a second distillation), resulting is a first stream comprising triglycerides 156, and a second stream comprising a free fatty acids distillate 158. For example, this process can be used to separate the fatty acids, glycerol, and triglyceride products. In one example, after concentrating at 106, the resulting concentrated mix of fatty acids and triglycerides 152 may comprise a variety of fatty acids at a variety of concentrations. For example, the concentrated mix of fatty acids and triglycerides 152 can comprise an approximately fifty/fifty mix of free fatty acids and triglycerides, and one-percent or less water. In some implementation, the free fatty acids may include palmitic acid (e.g., at a concentration from about five percent to about thirty percent), steric acid (e.g., at a concentration from about seventy percent to about ninety-five percent), and other fatty acids.

In this implementation, the distillation process may utilize similar processes as described above, such as using a distillation tower or distillation column to concentrate the free fatty acids in a vapor phase; using a vacuum; and/or a vapor stream condensation method to concentrate the fatty acids. As an example, the vapor phase extracted from the distillation, can comprise the desired fatty acids, which can be cooled and condensed. The resulting product of the distillation and concentration can comprise a concentrated mix of fatty acids in the second stream of free fatty acids distillate 158. In one implementation, the free fatty acids distillate 158 can comprise a concentration of ninety-eight percent or greater free fatty acids. Further, in this implementation, the first stream comprises the triglycerides 156 that are separated from the free fatty acids.

In one aspect, the resulting free fatty acids distillate 158 may comprise different types and concentrations of fatty acids, such as palmitic and stearic, for example, depending on the feed stock source of plant-based fat emulsion 150. That is, for example, the type and concentrations of vegetable fat input to the exemplary process 100 can be determinative of the types and concentrations of free fatty acids distillate 158. In one implementation, the free fatty acids distillate 158 can comprise about ninety-eight percent or greater of free fatty acids. In another implementation, the free fatty acids distillate 158 can comprise about ninety-eight percent or less of free fatty acids.

In one implementation, in this aspect, the resulting concentrated free fatty acids distillate 158 can be examined and/or analyzed to identify a next processing step for the distillate 158. That is, for example, if the type and concentrations of vegetable fat feedstock (e.g., 150) is well known, an experienced processor may recognize that the concentrated free fatty acids distillate 158 is to be treated in a particular way. In one implementation, the concentrated free fatty acids distillate 158 can be subjected to analysis, such as using a gas chromatography, and/or combined with mass spectrometry analysis, or another analysis that may help identify the concentrations and types of free fatty acids available in the distillate 158 (e.g., liquid chromatography, capillary electrophoresis, ion-mobility spectrometry, chemical analysis, etc.). In this implementation, the results of the analysis may be determinative of the subsequent processing steps of the concentrated free fatty acids distillate 158.

For example, if the analysis (e.g., or direct observation) identifies a lower level (e.g., lower than a predetermined level desired for the target use) of palmitic acid (C16:0) the distillate may first go to a hydrogenation processing, described below at 110 in the exemplary method 100. Alternately, in this implementation, for example, if the analysis (e.g., or direct observation) identifies a higher level (e.g., higher than a predetermined level desired for the target use) of palmitic acid (C16:0) the distillate may go to a fractional distillation process, described below at 112 in the exemplary method 100. In this implementation, the analysis may identify different levels of other free fatty acids, which may trigger or determine the process flow of the distillate 158, such as to hydrogenation 110 first, or directly to fractional distillation 112.

In one implementation, in the exemplary method of FIG. 1, the concentrated free fatty acids distillate 158 may be subjected to a hydrogenation process, at 110. Hydrogenation can comprise a process that treats the feed distillate (158) with hydrogen, resulting in a chemical reaction between the molecular hydrogen and double carbon bonds between two carbon atoms in the fatty acid. That is, for example, some of the fatty acids in the concentrated free fatty acids distillate 158 may be unsaturated (e.g., monounsaturated or polyunsaturated). An unsaturated fatty acid comprises one or more sets of double bonds between two neighboring carbon atoms in the fatty acid chain; meaning that the chain is not fully saturated with hydrogen. In this implementation, the hydrogenation process can be used to convert some or all of the unsaturated fatty acids into saturated fatty acids, by converting at least some of the double carbon bonds into a bond with a hydrogen atom. In this way, the free fatty acids distillate 158 can comprise a higher number of saturated fatty acids (e.g., with hydrogen).

As an example, a common measurement to identify the amount saturation (e.g., and/or unsaturation) in a fatty acid, or mixture of fatty acids, is its iodine value. For example, the American Oil Chemists' Society has an official Iodine Value of Fatty Acids testing method, namely, Tg 1a-64, which uses the Wijs iodine method. This method can be used to identify the iodine value of a target product. Using this method, for example, the resulting iodine value can identify the amount of iodine in grams that are consumed by one-hundred grams of a fatty acid. A higher iodine number is indicative of a higher unsaturated fatty acid content (e.g., and lower saturated fat content); and a lower number is indicative of a higher saturated fatty acid content (e.g., and lower unsaturated fat content).

In one implementation, the hydrogenation 110 process may lower the iodine value of the hydrogenated FFA distillate 160, for example, by saturating the fatty acids with hydrogen—carbon bonds, and reducing the carbon-carbon double bonds. In one implementation, using the hydrogenation step 110, the iodine value may be reduced from a level of about 120 cg l/g or higher per sample (e.g., or 45-70 cg l/g) to a lower level of about 10 cg l/g or less (e.g., about 5 cg l/g or less) per sample. In another implementation, the iodine value may be reduced to a lower level of about 2.0 cg l/g or less per sample. Additionally, in another implementation, the iodine value may be reduced to a lower level of about 1.0 cg l/g or less per sample.

The hydrogenated FFA distillate 160 resulting from the hydrogenation 110 can comprise a variety of purity levels. In one implementation, as illustrated in FIG. 1, the hydrogenated FFA distillate 160 can be subjected to a fractional distillation process, at 112. In an alternate implementation, as illustrated in FIG. 1, and described above, at least a portion of the free fatty acids distillate 158 resulting from the separation distillation 108 (e.g., the second distillation) may proceed to the fractional distillation 112 (e.g., based on the analysis of the content of the free fatty acids distillate 158, described above). For example, if the palmitic acid levels in the free fatty acids distillate 158 are relatively high, the material may move to the fractional distillation process, at 112. Alternately, if the palmitic acid levels in the free fatty acids distillate 158 are relatively low, the material may move to the hydrogenation process, at 110, and subsequently to the fractional distillation process, at 112.

At 112, in one implementation, fractional distillation can be used to reduce (e.g., by removal) the amount of palmitic acid in the material fed to this process (e.g., free fatty acids distillate 158 and/or hydrogenated FFA distillate 160). In one implementation, fractional distillation can comprise using the different boiling points of the various components of the feed stock, under different operating pressures, to help remove an undesired component. As an example, a typical boiling point of palmitic acid is 351.0° C. (663.8° F.), and the typical boiling point of stearic acid is 375.2° C. (707.36° F.); thereby providing a difference of 24.2° C. (75.56° F.) between boiling points.

Figure 2:
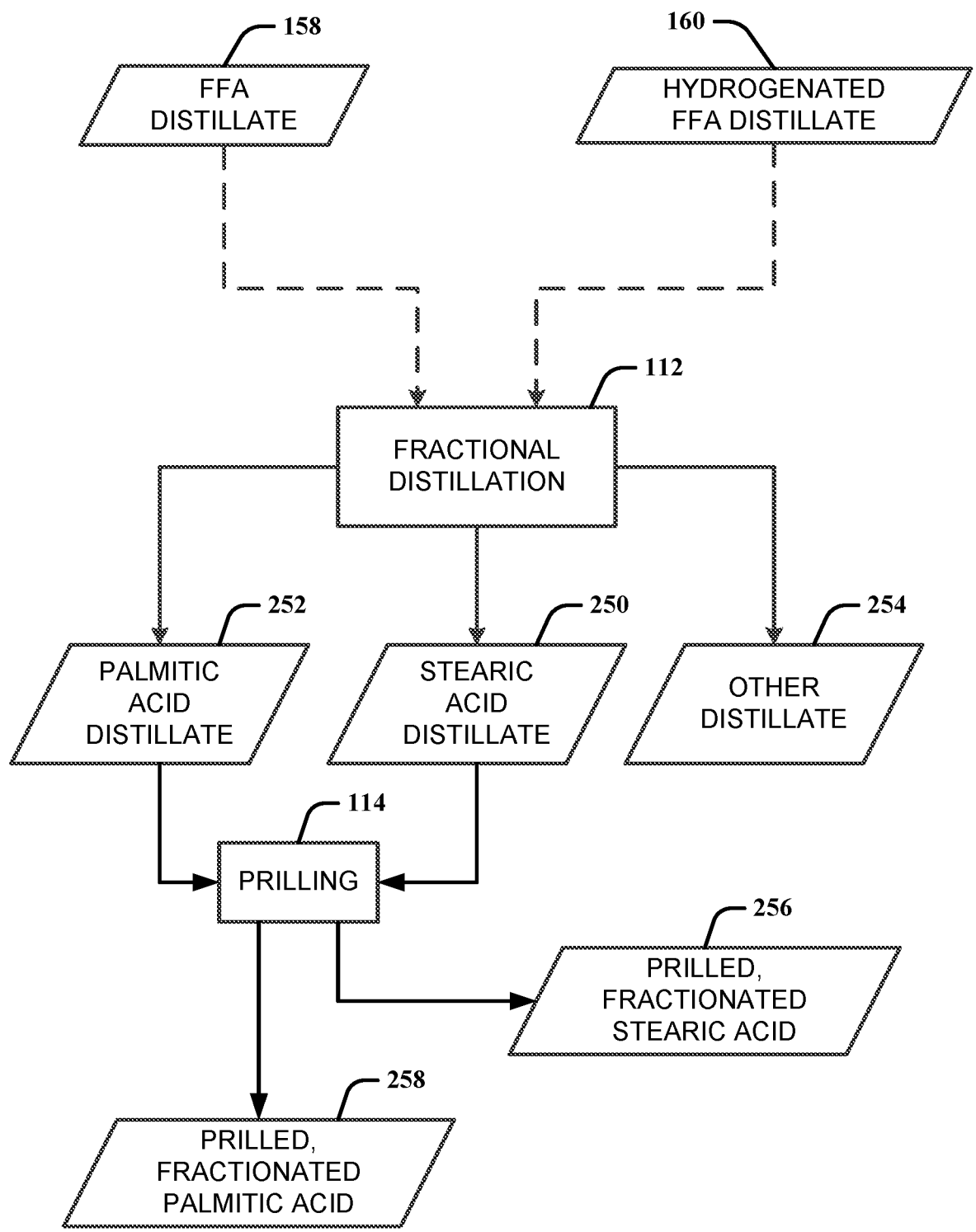
FIG. 2 is a flow diagram illustrating an exemplary implementation of a method for producing one or more products described herein.

Therefore, in one implementation, during fractional distillation, a first operating temperature can be maintained between the boiling point of palmitic acid and stearic acid in order to "boil off" (e.g., convert to palmitic acid distillate) at least a portion of the palmitic acid content. Further, a second operating temperature (e.g., higher temperature) can be maintained above the boiling point of stearic acid to "boil off" (e.g., convert to stearic acid distillate) at least a portion of the stearic acid content. As illustrated in FIG. 2, the fractional distillation process 112 can result in substantial separation of stearic acid content and palmitic acid content into separate product streams. That is, for example, a first distillate portion 252 may comprise high concentrations of palmitic acid, and a second distillate portion 250 may comprise higher concentrations of stearic acid. Additionally, the process may yield one or more other distillate products 254.

Further, for example, the distillation process can occur at a variety of operating pressures, such as from 50 to 150 millibar (mbar) (e.g., or <10 to 180 mbar) (0.73 to 2.18 pounds per square inch (PSI)—e.g., or <0.15 to 2.61 PSI). Decreasing the operating pressure can affect the operating temperature, or feed temperature, needed to reach a boiling point (e.g., lower pressure can result in a lower temperature needed). Therefore, in one implementation, lowering the pressure in a fractional distillation vessel, for example, can result in the distillation (e.g., palmitic acid and stearic acid "boil off") at a lower operating temperature. As an example, the feed temperature (e.g., and operating temperature) and feed pressure may affect the purity of the resulting stearic acid in the resulting fractionated free fatty acid product. Therefore, in one implementation, achieving a desirable feed pressure can result in a desired purity, for example, if the feed temperature is less variable. Further, differences in the boiling points of the constituents of the feed stock to the fractional distillation process can also affect the separation efficiency. For example, a higher variety of constituents in the feed stock may have an effect of the purity of the resulting product stream(s).

In one implementation, as illustrated in FIG. 2, at least one of products (e.g., product streams) resulting from the fractional distillation 112 process can comprise concentrated stearic acid 250 in the form of free-fatty acids. In one implementation, the concentrated stearic acid 250 can comprise more than about 80% stearic acid by weight. In one implementation, the fractional distillation 112 process of the free fatty acids distillate 158 and/or hydrogenated FFA distillate 160, described herein may occur through a continuous process to produce the concentrated stearic acid 250 product. In another implementation, the fractional distillation 112 of the free fatty acids distillate 158 and/or hydrogenated FFA distillate 160, described above, may occur through a batch process to produce the concentrated stearic acid product 250. During the fractional distillation 112, more than about 90% stearic acid by weight may be separated from the palmitic acid distillate 252. In one implementation, the palmitic acid product 252 can be separated from the concentrated stearic acid 250 product, and used as a separate product (e.g., concentrated vegetable-based palmitic acid).

As illustrated in FIG. 1, at 114, the concentrated stearic acid 250 product (e.g., and/or the palmitic acid product 252) may undergo prilling. Prilling the concentrated stearic acid 250 product (e.g., and/or the palmitic acid product 252), from FIG. 2, can result in a prilled, fractionated vegetable-based fatty acid 162 (e.g., comprising concentrated stearic acid and/or palmitic acid). In one implementation, the prilling process 114 can result in a pelletized version of a material, for example, a small aggregate or globule of the material, typically comprising a relatively solid sphere, which can be formed from a heated liquid. The prilled product 162 may provide for easier handling in certain applications.

As an example, during the prilling process 114, a liquid form of the fatty acid 150 (e.g., heated up to approximately 10° F. above the melting point of the fatty acid) can be introduced into a chamber that is disposed at a desired prilling temperature; where the desired temperature allows the liquid to solidify into a small aggregate or globule of prilled fatty acid 162. For example, a desired prilling temperature (e.g., in a prilling chamber) may comprise about 30° to about 50° Fahrenheit (e.g., about −1.1° to about 10° Celsius). Further, in one implementation, the prilling chamber may comprise a countercurrent (e.g., counter to the flow of an introduced stream of the liquid fatty acid) of air flow, which may also be chilled to the desired prilling temperature. In this example, the liquid fatty acid can be introduced substantially at a top of a chilled prilling chamber (e.g., tower), a chilled air flow can be introduced to the chamber, resulting in formation of the prilled fatty acid 162.

As another example, the prilling method may be different for different fatty acids. In one implementation, because palmitic acid (e.g., the palmitic distillate stream 252) has a lower melting point that stearic acid (e.g., the stearic acid distillate stream 250), the injection, or spraying temperature of a palmitic acid concentrate 252 into the prilling chamber can be lower than that for the stearic acid concentrate 250. In one implementation, in FIG. 2, the stearic acid concentrate 250 provided after the fractional distillation 112 may undergo prilling 114, resulting in prilled stearic acid 256. In another implementation, the palmitic acid concentrate 252 provided after the fractional distillation 112 may undergo prilling 114, resulting in prilled palmitic acid 258.

In one implementation, the prilled stearic acid 256 may be rubber grade stearic acid. In another implementation, the prilled stearic acid 256 produced may be at least 90% stearic acid. In another implementation, the prilled stearic acid 256 produced may be at least 80% stearic acid. In yet another implementation, the prilled stearic acid 256 produced may be at least 70% stearic acid.

In one implementation, the fractional distillation may yield a concentrated palmitic acid product 252 that comprises more than about 80% palmitic acid by weight. In one implementation, the fractional distillation 112 of the free fatty acids distillate 158 and/or hydrogenated FFA distillate 160, described above, may occur through a continuous process to produce the concentrated palmitic acid product 252. In another implementation, the fractional distillation 112 of the free fatty acids distillate 158 and/or hydrogenated FFA distillate 160, described above, may occur through a batch process to produce the concentrated palmitic acid product 252. During the fractional distillation 112, more than about 90% stearic acid by weight may be separated from the palmitic acid. In one implementation, stearic acid 150 may be separated from the palmitic acid 220 after the fractional distillation 112 and provided as a separate product, as shown in FIG. 2.

Figure 3:
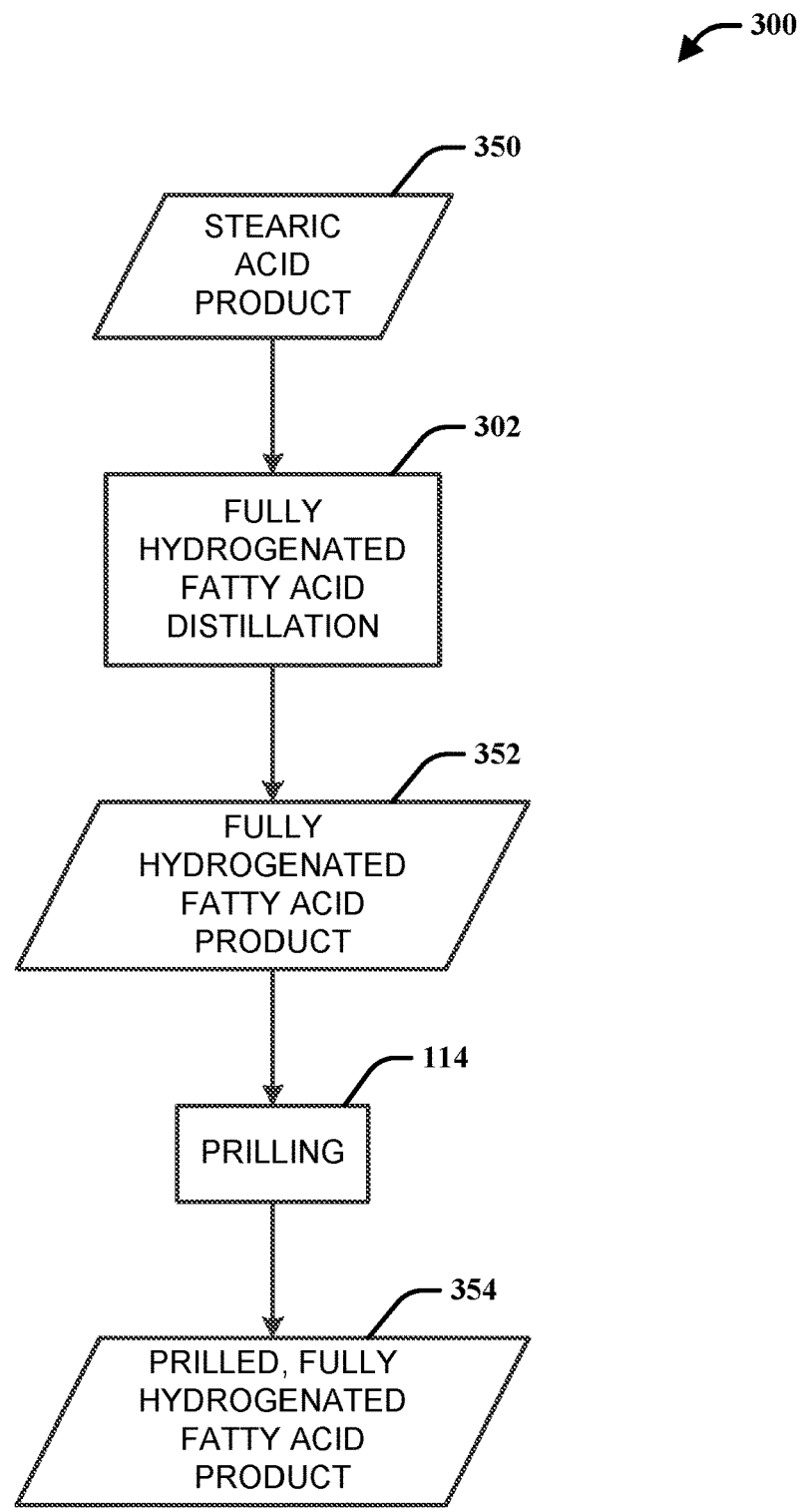
FIG. 3 is a flow diagram illustrating an exemplary implementation of a method for producing one or more products described herein.

In one implementation, in FIG. 3, a concentrated stearic acid product 350 may be further distilled to produce fully hydrogenated fatty acids 352. In one implementation, fully hydrogenated fatty acid 352 may result from distilling the stearic acid, at 302, and separating fully hydrogenated fatty acid 352 from the stearic acid 350 product. In this implementation the distillation to separate the fully hydrogenated fatty acid 352 may be referred to as the fully hydrogenated fatty acid distillation 302. As an example, fully hydrogenated fatty acids 352 are saturated fats that contain no trans-fats. In one implementation, fully hydrogenated fatty acids 352 may include one or more of the following fatty acids: caprylic acid, capric acid, lauric acid, myristic acid, palmitic acid, stearic acid, arachidic acid, behenic acid, lignoceric acid, and cerotic acid. In another implementation, the fully hydrogenated fatty acids 352 may include a combination of one or more of the following fatty acids: caprylic acid, capric acid, lauric acid, myristic acid, palmitic acid, stearic acid, arachidic acid, behenic acid, lignoceric acid, and cerotic acid.

In one implementation, the concentrated stearic acid product 350 may be subjected to fully hydrogenated fatty acid distillation 302 though a distillation process, for example, under a high vacuum (e.g., low operating pressure). In one implementation, the fully hydrogenated fatty acid distillation 302 may occur at a temperature at least about 400° F. (200° C.). In one implementation, a fully hydrogenated fatty acid product 352 may be a result of the fully hydrogenated fatty acid distillation 302.

In one implementation, the fully hydrogenated fatty acid distillation 302 may result in a fully hydrogenated fatty acid product 352 that comprises about ninety-nine percent fully hydrogenated fatty acid (e.g., ~99% saturated fatty acid). In another implementation, the fully hydrogenated fatty acid distillation 302 may result in a fully hydrogenated fatty acid 352 that comprises about ninety-eight percent fully hydrogenated fatty acid (e.g., ~98% saturated fatty acid).

As an example, fully hydrogenated fatty acids 352 may be used as a food source or for other commercial uses. In one implementation, the fully hydrogenated fatty acids 352 may be used for alternate applications (e.g., as an ingredient in food for humans). In another implementation, the hydrogenated fatty acids 352 may be used in animal feed applications.

Additionally, fully hydrogenated fatty acid 352 may be provided in prill form. In one implementation, the fully hydrogenated fatty acid 352 may undergo the prilling 114 process to provide a prilled fully hydrogenated fatty acid 354.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A process for producing a vegetable-based stearic acid product from a vegetable-based product comprising:
   drying a vegetable-based fat emulsion resulting in a fatty acid and triglyceride mix;
   distilling the fatty acid and triglyceride mix to substantially separate the triglycerides from free fatty acids; and
   separating the free fatty acids into one or more types of fatty-acids, resulting in a concentrated fatty acid vegetable-based stearic acid product.

2. The process of claim 1, the drying a vegetable-based fat emulsion comprising subjecting the vegetable-based fat emulsion to a steam distillation process, resulting in a dryer vegetable fat that has also been deodorized.

3. The process of claim 1, comprising concentrating the fatty acid and triglyceride mix prior to the distilling of the fatty acid and triglyceride mix resulting in a concentrated fatty acid and triglyceride mix, and the distilling comprising distilling the concentrated fatty acid and triglyceride mix.

4. The process of claim 1, the separating the free fatty acids into one or more types of fatty-acids comprising subjecting the free fatty acids to fractional distillation.

5. The process of claim 1, comprising prilling the fatty acid vegetable-based stearic acid product, resulting in a prilled vegetable-based stearic acid.

6. The process of claim 1, the separating the free fatty acids into one or more types of fatty-acids, resulting in palmitic acid distillate and stearic acid distillate.

7. The process of claim 6, comprising one or more of:
   prilling the palmitic acid distillate resulting in prilled fractionated palmitic acid; and
   prilling the stearic acid distillate resulting in prilled fractionated stearic acid.

8. The process of claim 1, comprising hydrogenating the free fatty acids prior to separating the free fatty acids into one or more types of fatty-acids resulting in hydrogenated free fatty acid distillate.

9. The process of claim 8, comprising subjecting the hydrogenated free fatty acid distillate to fractional distillation resulting in hydrogenated palmitic acid distillate and hydrogenated stearic acid distillate.

10. The process of claim 1, comprising subjecting the vegetable-based stearic acid product to fully hydrogenated fatty acid distillation resulting in a fully hydrogenated, fatty acid, vegetable-based stearic acid product.

11. The process of claim 10, comprising prilling the fully hydrogenated, fatty acid, vegetable-based stearic acid product, resulting in a prilled, fully hydrogenated, fatty acid, vegetable-based stearic acid product.

12. The process of claim 1, the resulting fatty acid vegetable-based stearic acid product comprising a rubber grade stearic acid.

13. The process of claim 1, the resulting fatty acid vegetable-based stearic acid product comprising at least ninety percent stearic acid.

14. The process of claim 1, the vegetable-based fat emulsion provided as an emulsion feedstock to the drying, the emulsion feedstock comprising a combination of a vegetable oil-based feedstock and a vegetable-based feedstock.

15. The process of claim 14, the vegetable oil-based product comprising one or more of:
    soybean oil;
    corn oil;
    palm oil;
    coconut oil; and
    canola oil.

16. The process of claim 14, the vegetable-based product comprising one or more of:
    vegetative matter;
    seeds;
    fruits;
    flowers;
    grasses;
    vegetables; and
    roots.

17. The process of claim 1, comprising providing the vegetable-based fat emulsion as an emulsion feedstock to the drying, wherein the providing comprises one of:
    a batch process; and
    a continuous process.

18. The process of claim 17, the providing the vegetable-based fat emulsion to the drying comprising altering an amount or respective products comprised in the emulsion feedstock based at least upon a type of product comprised in the emulsion feedstock.

19. A method for producing a vegetable-based stearic acid product from a vegetable-based product comprising:
    providing a vegetable-based fat emulsion feedstock comprising a combination of a vegetable oil-based feedstock and a vegetable-based feedstock;
    drying and deodorizing the emulsion feedstock resulting in a dryer fatty acid and triglyceride mix;
    concentrating the fatty acid and triglyceride mix resulting in a concentrated fatty acid and triglyceride mix;
    distilling the concentrated fatty acid and triglyceride mix to substantially separate the triglycerides from free fatty acids;
    hydrogenating the free fatty acids resulting in hydrogenated free fatty acid distillate; and separating the free fatty acids into at least one or more types of fatty-acids, comprising subjecting the free fatty acids to fractional distillation, resulting in a concentrated fatty acid vegetable-based stearic acid product.

20. The method of claim 19, the concentrated fatty acid vegetable-based stearic acid product comprising a concentrated stearic acid distillate, and comprising prilling the concentrated stearic acid distillate, resulting in a prilled vegetable-based stearic acid product.

* * * * *